United States Patent [19]

Vane et al.

[11] 4,211,782
[45] Jul. 8, 1980

[54] PHARMACEUTICAL COMBINATION

[76] Inventors: John R. Vane, 7 White Angles, Beech Dell, Keston, Kent; Salvador Moncada, 17 St. David's Close, West Wickham, Kent both of England

[21] Appl. No.: 841,049

[22] Filed: Oct. 11, 1977

[30] Foreign Application Priority Data

Oct. 12, 1976 [GB] United Kingdom ............... 42280/76

[51] Int. Cl.² .................... A61K 31/44; A61K 31/47; A61K 31/455; A61K 31/415

[52] U.S. Cl. .................................. 424/263; 424/258; 424/266; 424/273 R; 424/284; 424/304; 424/311; 424/312; 424/314; 424/317; 424/330

[58] Field of Search ............... 424/263, 266, 273, 311, 424/314, 317, 183, 284, 258, 304, 312, 330

[56] References Cited

U.S. PATENT DOCUMENTS

| | | | |
|---|---|---|---|
| 2,999,049 | 9/1961 | Link | 424/183 |
| 3,903,266 | 9/1975 | Robbins | 424/183 |
| 3,932,656 | 1/1976 | Ramwell et al. | 424/183 |

FOREIGN PATENT DOCUMENTS

| | | | |
|---|---|---|---|
| 851122 | 8/1977 | Belgium | 424/317 |
| 2405M | 3/1964 | France | 424/183 |
| 3552M | 9/1965 | France | 424/183 |

OTHER PUBLICATIONS

*Nature*, vol. 263, No. 5579, pp. 663–665, 10/21/76.
*Tetrahedron Letters*, No. 30, pp. 2627–2628, 1977.
*Tetrahedron Letters*, No. 32, pp. 2805–2808, 1977.
*Prostaglandins*, Apr. 1977, vol. 13, No. 4, 611–619.
*Nature*, vol. 267, Jun. 16, 1977, 627 & 628.

*Primary Examiner*—Frederick E. Waddell
*Attorney, Agent, or Firm*—Donald Brown

[57] ABSTRACT

Combinations comprising an anti-aggregatory substance together with one or more of an anti-oxidant and a thromboxane A₂ synthetase inhibitor are disclosed. Combinations are useful for the treatment/prophylaxis of disorders attributable to blood platelet aggregation.

38 Claims, No Drawings

PHARMACEUTICAL COMBINATION

The present invention relates to a novel combination comprising an anti-aggregatory substance, an anti-oxidant and/or a thromboxane $A_2$ synthetase inhibitor, a formulation containing such a combination, a method of preparing such formulations, and to the use of the combination in medicine.

The Applicants have discovered a naturally occuring prostaglandin, prostacyclin ($PGI_2$; PGX) having the structure shown in formula (I) below (X=OH) which is implicated in the biological mechanisms giving rise to intravascular thrombosis, gastrointestinal disorders, vasodilation, and bronchodilation. They have also found how certain enzymes and other naturally occuring substances are implicated in the enzymic processes associated with the formation of PGX in body tissues, and as a result of these discoveries now provide a combination of substances useful in the prophylaxis or treatment of the above conditions.

PGX is located in a variety of body tissues including vascular, lung and stomach tissues. The notable biological property of PGX is its anti-aggregatory action on blood platelets at low concentrations, a property shared by other compounds, including those of formula (II) hereinbelow.

The metabolic relationship of PGX to other prostaglandins is believed to be that shown in the following chart:

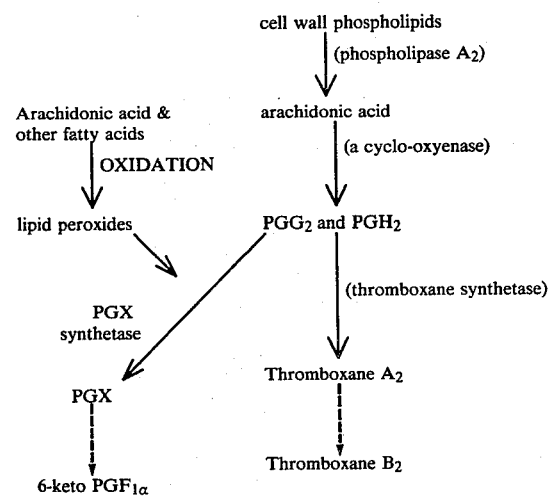

The prostaglandin endoperoxides ($PGG_2$ and $PGH_2$) are produced from arachidonic acid by a cyclo-oxygenase enzyme, and are converted both into PGX by PGX synthetase and into thromboxane $A_2$ by thromboxane synthetase. While PGX has potent anti-aggregatory activity, thromboxane $A_2$ is pro-aggregatory, and the inhibition of thromboxane synthetase would both stimulate the formation of PGX and prevent the formation of thromboxane $A_2$.

Arachidonic acid and other fatty acids undergo oxidation in the blood to produce lipid peroxides which inhibit the formation of PGX by the enzyme PGX synthetase. The use of an anti-oxidant to minimise the formation of lipid peroxides would in turn minimise the inhibition of PGX synthetase and promote the formation of the anti-aggregatory PGX.

The present invention accordingly provides a combination of substances (hereinafter referred to as "the Combination") which promote anti-aggregatory action on blood platelets comprising:

(a) an anti-aggregatory substance (as herein defined) together with (b) one or more of an antioxidant and a thromboxane $A_2$ synthetase inhibitor.

By an "anti-aggregatory substance" is meant a substance whose mode of action is similar to that of the anti-aggregatory action of PGX itself, one of the most notable features of which is the ability to reverse platelet aggregation and degrade existing thrombi.

Amongst the compounds which may be used in the combination of the present invention as anti-aggregatory substances are compounds of formula (I).

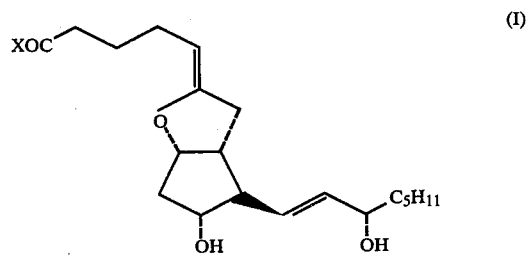

wherein X is $OR^1$ or $NHR^2$ and $R^1$ is hydrogen, alkyl or a pharmaceutically acceptable cation and $R^2$ is hydrogen or alkyl.

Also amongst the compounds which may be used in the combination of the invention as anti-aggregatory substances are compounds of formula (II)

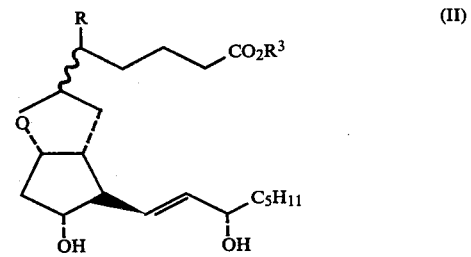

in which R is hydrogen, hydroxy, halo, cyano, amino, nitro, acyloxy or alkyl and $R^3$ is hydrogen, alkyl or a pharmaceutically acceptable cation.

In the above alkyl has 1 to 4 carbon atoms and halo represents iodo, bromo or chloro.

Included amongst the compounds of formula (I) and formula (II) are:

Prostacyclin ((I), X=OH);
Prostacyclin sodium salt ((I), X=ONa);
Prostacyclin methyl ester ((I), X=OMe); and
Dihydroprostacyclin [(II), $R=R^3=H$; 9-deoxy-6S-9α-epoxy $PGF_{1α}$]

Compounds of formula (I) or (II) may be prepared by the methods described by Johnson et al J. Amer. Chem. Soc., 1977, 99, 4182. Compounds of formula (I) may also be prepared by the method of Whittaker, Tet. Letters, 1977, 2805. Prostacyclin (PGX) may also be prepared biosynthetically as described by Moncada et al, Nature, 1976, 763, 663.

The following compounds are suitable thromboxane $A_2$ synthetase inhibitors:

imidazole, 1-methylimidazole, benzydamine or a compound of formula (III):

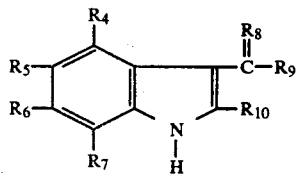

wherein

R$_4$ and R$_7$, are the same or different and each represents hydrogen or alkyl;

R$_5$ represents hydrogen, alkyl, chloro or methoxy;

R$_6$ represents hydrogen, alkyl or chloro;

R$_8$ represents an oxygen atom or the group NH=; and

R$_9$ represents 2, 3 or 4-pyridyl or the corresponding N-oxide derivative thereof.

R$_{10}$ represents hydrogen, alkyl, cyclohexyl, phenyl, 4-fluorophenyl, 4-chlorophenyl or 4-methoxyphenyl;

A particularly valuable compound of formula (III) in respect of its thromboxane A$_2$ synthetase inhibitory properties, is the following:

3-(2-isopropyl)-indolyl-3-pyridyl ketone.

The compounds of formula (III) may be made as described in U.K. Patent Specification No. 1,318,300.

Suitable anti-oxidants for use in the present invention are as follows:

α-tocopherol nicotinate;

NN'-diphenyl-p-phenylenediamine; Vitamin A, Vitamin C, Vitamin E and analogues thereof known in the art; 6-ethoxy-1,2-dihydro-2,2,4-trimethylquinoline; Retinol palmitate; and other suitable anti-oxidants known in the art as food additives such as the gallates.

(See for example: Dry J., et al. Rev. Prat., 1973, 23/59, 5263–5268; Korsan-Bengtsen L., et al., Thrombos. Diothes. haemorrh (Stuttg), 1974, 31, 505; and Washburn J.H., The Gerontologist, 1973, p. 436).

The Combination is useful wherever is it desired to inhibit platelet aggregation, to reduce the adhesive character of platelets, and to treat or prevent the formation of thrombi in mammals, including man. For example, the Combination is useful in the treatment and prevention of myocardial infarcts, to treat and prevent post-operative thrombosis, to promote patency of vascular grafts following surgery, and to treat complications of arteriosclerosis and conditions such as atherosclerosis, blood clotting defects due to lipemia, and other clinical conditions in which the underlying etiology is associated with lipid imbalance or hyperlipidemia.

The Combination is useful as an additive to blood, blood products, blood substitutes, and other fluids which are used in artificial extra-corporeal circulation and perfusion of isolated body portions, e.g., limbs and organs, whether attached to the original body, detached and being preserved or prepared for transplant, or attached to a new body. It may also be used in laboratory animals, e.g., cats, dogs, rabbits, monkeys and rats, for these purposes in order to develop new methods and techniques for organ and limb transplants.

While it is preferred to administer the Combination as a mixture of ingredients for the purposes indicated above, the ingredients may be administered concurrently or sequentially, either as the raw chemicals or separate pharmaceutical formulations of each ingredient.

The Combination is useful in mammals, including man, to reduce and control excessive gastric secretion, thereby reducing or avoiding gastrointestinal ulcer formation, and accelerating the healing of such ulcers already present in the gastrointestinal tract.

The Combination also exhibits a vasodilatory action on blood vessels and therefore has a particular utility as an anti-hypertensive for the treatment of high blood pressure in mammals, including man. The Combination affects the biochemical co-operation between platelets and vascular endothelium which contributes to the repair of vascular endothelium, and may be used to promote wound healing in mammals, including man.

The Combination exhibits a dilatory action on the bronchi and therefore has a particular utility as a bronchodilator for the treatment or prophylaxis of bronchitis and bronchial asthma in mammals including man.

The Combination preferably contains an anti-aggregatory substance in the range of 25% to 75% (w/w), an antioxidant in the range of 10% to 50% (w/w) and a thromboxane A$_2$ synthetase inhibitor in the range of 10% to 75% (w/w).

When the Combination contains only an anti-aggregatory substance and an antioxidant, the anti-aggregatory substance is preferably in the range of 10% to 90% (w/w), and the anti-oxidant in the range of 10% to 90% (w/w). When the Combination only contains an anti-aggregatory substance and a thromboxane A$_2$ synthetase inhibitor, the anti-aggregatory substance is preferably in the range of 10% to 75% (w/w), and the inhibitor is in the range of 25% to 90% (w/w).

The amount of the Combination required (hereinafter referred to as the active ingredient) for therapeutic effect will vary with the route of administration, and the nature of the condition under treatment. In general a suitable dose for a mammal of the Combination will lie in the range of 0.5 to 300 mg. per kg. body weight.

While it is possible for the Combination to be administered as a simple mixture of components it is preferable to present it as a pharmaceutical formulation. The formulations, both for veterinary and for human medical use, of the present invention comprise the active ingredient, as above defined, together with one or more acceptable carriers therefor and optionally other therapeutic ingredients. The carrier(s) must be 'acceptable' in the sense of being compatible with the other ingredients of the formulation and not deleterious to the recipient thereof. Formulations which contain PGX or salts thereof are preferably non-aqueous and non-hydroxylic in nature. Unit doses or a formulation contain between 0.05 mg. and 1.5 g. of the active ingredient.

Formulations include those suitable for oral, rectal, vaginal, intrapulmonary or parenteral (including subcutaneous, intramuscular and intravenous) administration.

The formulations may conveniently be presented in unit dosage form and may be prepared by any of the methods well known in the art of pharmacy. All methods include the step of bringing in association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

According to the present invention there are therefore provided:-
(a) a combination comprising an anti-aggregatory substance together with one or more of an antioxidant and a thromboxane A₂ synthetase inhibitor;
(b) the preparation of such a combination by admixture of the components;
(c) a pharmaceutical formulation containing the combination;
(d) the preparation of such pharmaceutical formulations;
(e) method for the treatment and/or prophylaxis of thrombosis in a mammal or mammalian tissues, including man comprising the administration of a non-toxic, treatment or prophylactic anti-thrombotic amount of the combination;
(f) method for inducing vasodilation in a mammal, including man comprising the administration of a non-toxic, vasodilatory amount of the combination;
(g) method for the prophylaxis and/or treatment of gastric lesions in a mammal, including man comprising the administration of a non-toxic, prophylactic or treatment amount of the combination;
(h) method for the treatment of wounds in a mammal, including man comprising the administration of a non-toxic, wound-treatment amount of the combination;
(i) method for inducing bronchodilation in a mammal, including man comprising the administration of a non-toxic, bronchodilatory amount of the combination;

The following Example is provided by way of an illustration of the present invention and should in no way be construed as constituting a limitation thereof.

EXAMPLE 1

Tablets containing the following ingredients were prepared by standard procedures of pharmacy:-

| (a) | Dihydroprostacyclin | 200 mg |
| --- | --- | --- |
|  | Imidazole | 200 mg |
|  | Vitamin E | 100 mg |
| (b) | Prostacyclin methyl ester | 450 mg |
|  | 3-(2-isopropyl)-indolyl-3-pyridyl ketone | 450 mg |
|  | α-tocophenol nicotinate | 100 mg |
| (c) | Dihydroprostacyclin | 200 mg |
|  | Imidazole | 300 mg |
| (d) | Prostacyclin methyl ester | 800 mg |
|  | 6-Ethoxy-1,2-dihydro-2,2,4-trimethyl-quinoline | 200 mg |

What is claimed is:

1. A combination of substances which are in an amount effective to promote an anti-aggregatory action on blood platelets comprising:
   (a) an anti-platelet aggregatory substance, an
   (b) one or more of (i) an anti-oxidant able to minimize formation of lipid peroxides, and (ii) an inhibitor of thromboxane A₂ synthetase.
2. A combination according to claim 1 comprising:
   (a) an anti-aggregatory substance;
   (b) an anti-oxidant; and
   (c) a thromboxane A₂ synthetase inhibitor.
3. A combination according to claim 1 comprising:
   (a) an anti-aggregatory substance; and
   (b) an anti-oxidant.
4. A combination according to claim 1 comprising:-
   (a) an anti-aggregatory substance; and
   (b) a thromboxane A₂ synthetase inhibitor.

5. A combination according to claim 1 wherein the anti-aggregatory substance is a compound of formula (I)

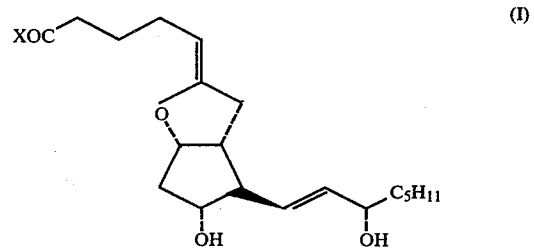

(I)

wherein X is selected from the group consisting of $OR^1$ and $NHR^2$; $R^1$ is selected from the group consisting of hydrogen, alkyl and a pharmaceutically acceptable cation and $R^2$ is selected from the group consisting of hydrogen and alkyl.

6. A combination according to claim 5 wherein, in the compound of formula (I), X is $OR^1$ and $R^1$ is hydrogen.
7. A combination according to claim 5 wherein, in the compound of formula (I), Y is $OR^1$ and $R^1$ is Na.
8. A combination according to claim 5 wherein, in the compound of formula (I), X is $OR^1$ and $R^1$ is $CH_3$.
9. A combination according to claim 1 wherein the anti-aggregatory substance is a compound of formula (II)

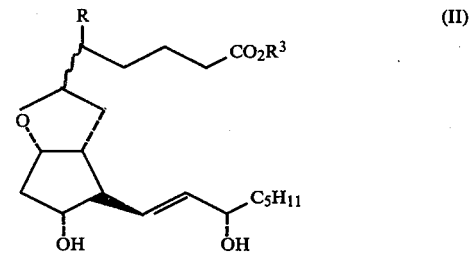

(II)

wherein R is selected from the group consisting of hydrogen, hydroxy, halo, cyano, amino, nitro, acyloxy and alkyl and $R^3$ is selected from the group consisting of hydrogen, alkyl and a pharmaceutically acceptable cation.

10. A combination according to claim 9 wherein the anti-aggregatory substance is 9-deoxy-6S-9α-epoxy $PGF_{1α}$.
11. A combination according to claim 1 wherein the anti-oxidant is selected from the group consisting of α-tocopherol nicotinate; NN'-diphenyl-p-phenylenediamine; Vitamin A; Vitamin C; Vitamin E; 6-ethoxy-1,2-dihydro-2,2,4-trimethylquinoline and Rentinol palmitate.
12. A combination according to claim 1 wherein the thromboxane A₂ synthetase inhibitor is selected from the group consisting of imidazole, 1-methylimidazole, benzydamine and a compound of the formula (III)

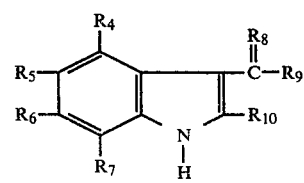

in which R⁴ and R⁷ are the same or different and are selected from the group consisting of hydrogen and alkyl; R⁵ is selected from the group consisting of hydrogen, alkyl, chloro and methoxy; R⁶ is selected from the group consisting of hydrogen, alkyl and chloro; R⁸ is selected from the group consisting of an oxygen atom and the group HN≡; R⁹ is selected from the group consisting of 2, 3 or 4 pyridyl and the corresponding N-oxides thereof; and R¹⁰ is selected from the group consisting of hydrogen, alkyl, cyclohexyl, phenyl, 4-fluorophenyl, 4-chlorophenyl and 4-methoxyphenyl.

13. A combination according to claim 12 wherein the thromboxane A₂ synthetase inhibitor is 3-(2-isopropyl)-indolyl-3-pyridyl ketone.

14. A pharmaceutical formulation comprising the combination of claim 1 together with a pharmaceutically acceptable carrier therefor.

15. A formulation according to claim 14 wherein the carrier is a solid.

16. A formulation according to claim 14 wherein the carrier is a liquid.

17. A formulation according to claim 14 in a form suitable for oral, parenteral, rectal, vaginal or intrapulmonary administration.

18. A formulation according to claim 14 in tablet form.

19. A formulation according to claim 14 in unit dosage form.

20. A formulation according to claim 19 containing from 0.05 mg to 1.5 g of total active ingredient.

21. A method for the treatment or prophylaxis of thrombosis in a mammal or a mammalian tissue comprising the administration to the mammal or the tissue of a non-toxic, treatment or prophylactic anti-thrombotic effective amount of the combination of claim 1.

22. A method for inducing vasodilation in a mammal comprising the administration to a mammal of a non-toxic, vasodilatory effective amount of the combination of claim 1.

23. A method for the prophylaxis or treatment of gastric lesions in a mammal comprising the administration to the mammal of a non-toxic, prophylactic or treatment effective amount of the combination of claim 1.

24. A method for the promotions of wound healing in a mammal comprising administration to the mammal of a non-toxic, wound treatment effective amount of the combination of claim 1.

25. A method of inducing bronchodilation in a mammal comprising the administration of a non-toxic, bronchodilatory effective amount of the combination of claim 1.

26. A method according to claim 22 wherein the combination is administered in an amount of from 0.5 to 300 mg of total active ingredient per kilogram body weight.

27. A combination according to claim 1 in which the anti-aggregatory substance is itself present in an anti-thromboembolic treatment or prophylaxis effective amount.

28. A combination according to claim 1 in which the anti-oxidant is present in an amount effective to inhibit the formation of lipid peroxides.

29. A combination according to claim 1 in which the tromboxane A₂ synthetase inhibitor is itself present in an anti-thrombo-embolic treatment or prophylaxis effective amount.

30. A method according to claim 23 wherein the combination is administered in an amount of from 0.5 to 300 mg of total active ingredient per kilogram body weight.

31. A method according to claim 24 wherein the combination is administered in an amount of from 0.5 to 300 mg of total active ingredient per kilogram body weight.

32. A method according to claim 25 wherein the combination is administered in an amount of from 0.5 to 300 mg of total active ingredient per kilogram body weight.

33. A method for inducing vasodilation in a mammal comprising administration to the mammal of a non-toxic, vasodilatory effective amount of the combination of claim 7.

34. A method for the prophylaxis or treatment of gastric lesions in a mammal comprising administration to the mammal of a non-toxic, prophylactic or treatment effective amount of the combination of claim 7.

35. A method for the promotion of would healing in a mammal comprising administration to the mammal of a non-toxic, wound-treatment effective amount of the combination of claim 7.

36. A method of inducing bronchodilation in a mammal comprising the administration of a non-toxic, brochodilatory effective amount of the combination of claim 7.

37. A method for the treatment or prophylaxis of thrombosis in a mammal comprising the administration to the mammal of a non-toxic, treatment or prophylactic anti-thrombotic effective amount of the combination of claim 7.

38. A method according to claim 21 wherein the combination is administered in an amount of from 0.5 to 300 mg of total active ingredient per kilogram body weight.

* * * * *